Figure 1:
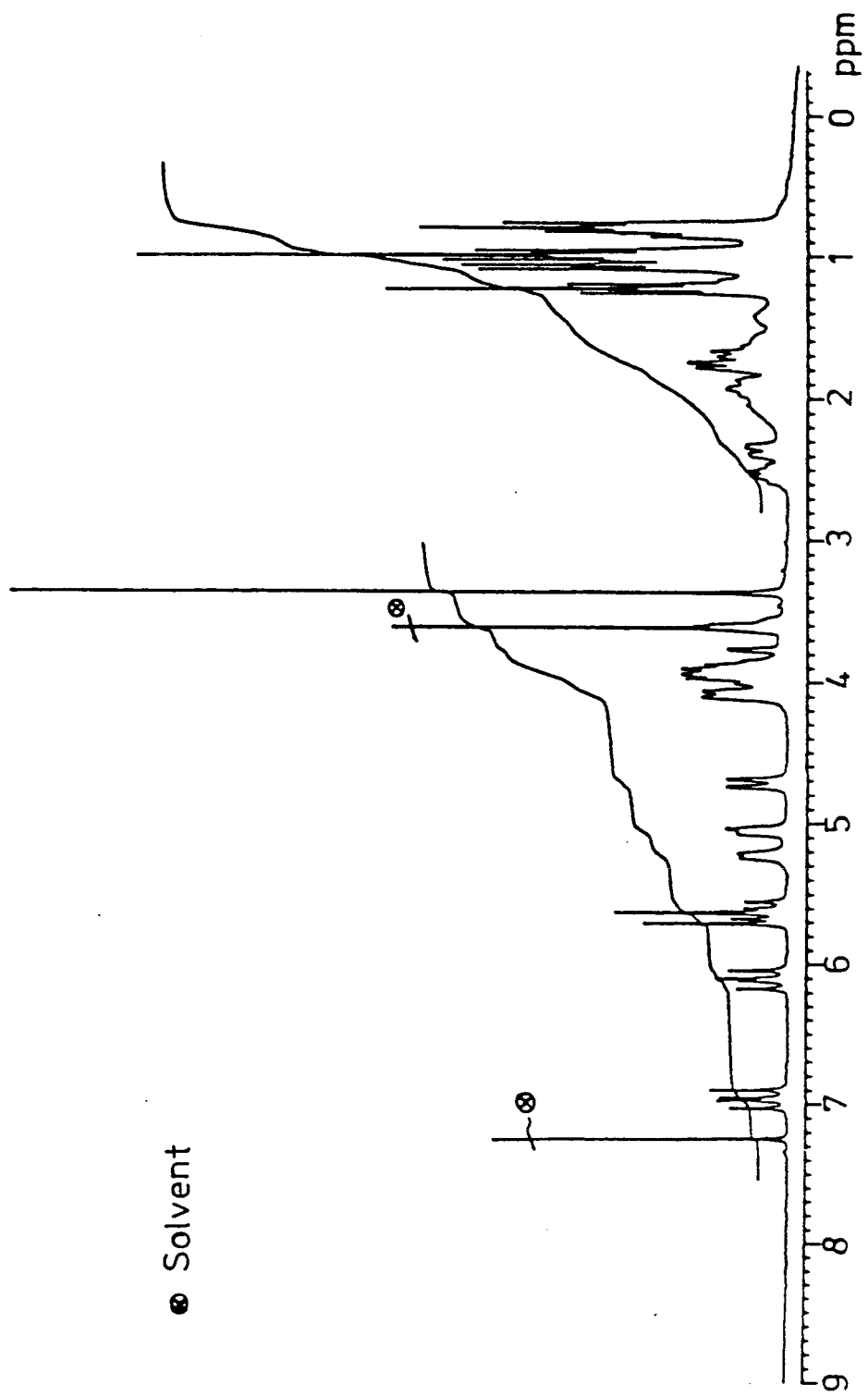

United States Patent [19]

Frobel et al.

[11] Patent Number: 5,073,369

[45] Date of Patent: Dec. 17, 1991

[54] EFOMYCINS AS PERFORMANCE PROMOTERS IN ANIMALS

[75] Inventors: Klaus Frobel; Erwin Bischoff, both of Wuppertal; Hartwig Müller, Velbert; Olga Salcher, Wuppertal; Anno De Jong, Wuppertal; Friedrich Berschauer, Wuppertal; Martin Scheer, Wuppertal, all of Fed. Rep. of Germany

[73] Assignee: Bayer Aktiengesellschaft, Leverkusen, Fed. Rep. of Germany

[21] Appl. No.: 840,638

[22] Filed: Mar. 17, 1986

[30] Foreign Application Priority Data

Mar. 30, 1985 [DE] Fed. Rep. of Germany ....... 3511753

[51] Int. Cl.$^5$ .................... A61K 35/00; A61K 31/70; A63L 1/00
[52] U.S. Cl. .................................. 424/121; 424/122; 426/2; 426/807; 514/253; 435/886
[58] Field of Search ................ 435/132, 886; 514/253; 424/121; 426/122, 807, 2

[56] References Cited

U.S. PATENT DOCUMENTS 3,076,746 2/1963 Arai ..................................... 435/898
4,132,778 1/1979 Hamill et al. ........................ 424/121

OTHER PUBLICATIONS

Chemical Abstracts 1986 vol. 104, pp. 320–321.
Polyether Antibiotics, vol. 1: Biology, pp., 6–21, and 106–119, edited by John W, Westley.

*Primary Examiner*—Douglas W. Robinson
*Assistant Examiner*—Irene Marx
*Attorney, Agent, or Firm*—Sprung Horn Kramer & Woods

[57] ABSTRACT

The present invention relates to the use of microbiologically prepared compounds and their mixtures, which are called efomycins, as performance promoters in farm animals and processes for their preparation, and furthermore new efomycins and their mixtures as new chemical compounds. The invention also relates to microorganisms which can be used for the preparation of the efomycins and their mixtures.

20 Claims, 11 Drawing Sheets

⊗ Solvent

⊗ Solvent

⊗ Solvent
△ TMS

⊗ Solvent
□ Impurity

Efomycin E

EFOMYCINS AS PERFORMANCE PROMOTERS IN ANIMALS

The present invention relates to the use of microbiologically prepared compounds and their mixtures, which are called efomycins, as performance promoters in animals and processes for their preparation, and furthermore new efomycins and their mixtures as new chemical compounds. The invention also relates to microorganisms which can be used for the preparation of the efomycins and their mixtures.

1. It has been found that efomycins A-F and their mixtures can be used as performance promoters in animals.

In addition, efomycins A-F and their mixtures exhibit powerful antimicrobial, such as, for example, antibacterial and antiviral, actions.

2. The new efomycins A, B, C, D and F with the chemical and physical properties described below and mixtures of these compounds have also been found:

2.1. The new compound efomycin A is characterized by the following chemical and physical properties:

1. The elemental analysis: C: 61.3-63.8, H: 8.2-9.4, O: 26.8-30.5.

It must be pointed out here that the margin of error of elemental analysis may be greater in the case of higher molecular weight naturally occurring substances than is generally customary (R. B. Woodward, Angew. Chem. 69, 50-51 (1957)).

2. The empirical formula: $C_{55}H_{90}O_{18}$.

3. The mass spectrum (Fast Atom Bombardment) molar mass + $Na^+$:1,061.

4. The $^1H$-nuclear magnetic resonance spectrum, given in parts per million, according to FIG. 1.

This was recorded in a WP 200 from Bruker at 200 MHz on a solution of efomycin A in deuterated chloroform with tetramethylsilane as the internal standard.

5. The $^{13}C$-nuclear magnetic resonance spectrum, given in parts per million, according to FIG. 2.

This was recorded in an EP 200 from Bruker at 50.32 MHz on a solution of efomycin A in deuterated chloroform with tetramethylsilane as the internal standard.

6. The UV absorption maximum at 251-254 nm in methanolic solution.

2.2. The new compound efomycin B is characterized by the following chemical and physical properties:

1. The elemental analysis: C: 61.3-63.8, H: 8.2-9.4, O: 26.8-30.5.

It must be pointed out here that the margin of error of elemental analysis may be greater in the case of higher molecular weight naturally occurring substances than is generally customary (R. B. Woodward, Angew. Chem. 69, 50-51 (1957)).

2. The empirical formula $C_{56}H_{92}O_{18}$. The mass spectrum (Fast Atom Bombardment).

3. Molar mass + $Na^+$:1,075.

4. The $^1H$-nuclear magnetic resonance spectrum, given in parts per million, according to FIG. 3. This was recorded in an EP 200 from Bruker at 200 MHz on a solution of efomycin B in deuterated chloroform with tetramethylsilane as the internal standard.

5. The $^{13}C$-nuclear magnetic resonance spectrum, given in parts per million, according to FIG. 4.

This was recorded in an EP 200 from Bruker at 50.32 MHz on a solution of efomycin B in deuterated chloroform with tetramethylsilane as the internal standard.

6. The UV absorption maximum at 251-254 nm in methanolic solution.

2.3. The new compound efomycin C is characterized by the following chemical and physical properties:

1. The empirical formula $C_{49}H_{80}O_{15}$.

2. The mass spectrum (Fast Atom Bombardment) molar mass + $Na^+$:931.

3. The $^1H$-nuclear magnetic resonance spectrum, given in parts per million, according to FIG. 5.

This was recorded in a WP 200 from Bruker at 200 MHz on a solution of efomycin C in deuterated chloroform with tetramethylsilane as the internal standard.

4. The $^{13}C$-nuclear magnetic resonance spectrum, given in parts per million, according to FIG. 6.

This was recorded in a WM 250 from Bruker at 250 MHz on a solution of efomycin C in deuterated chloroform with tetramethylsilane as the internal standard.

5. The UV absorption maximum at 251-254 nm in methanolic solution.

2.4. The new compound efomycin D is characterized by the following chemical and physical properties:

1. The empirical formula $C_{42}H_{68}O_{12}$.

2. The mass spectrum (Fast Atom Bombardment) molar mass + $Na^+$:787.

Figure 7:
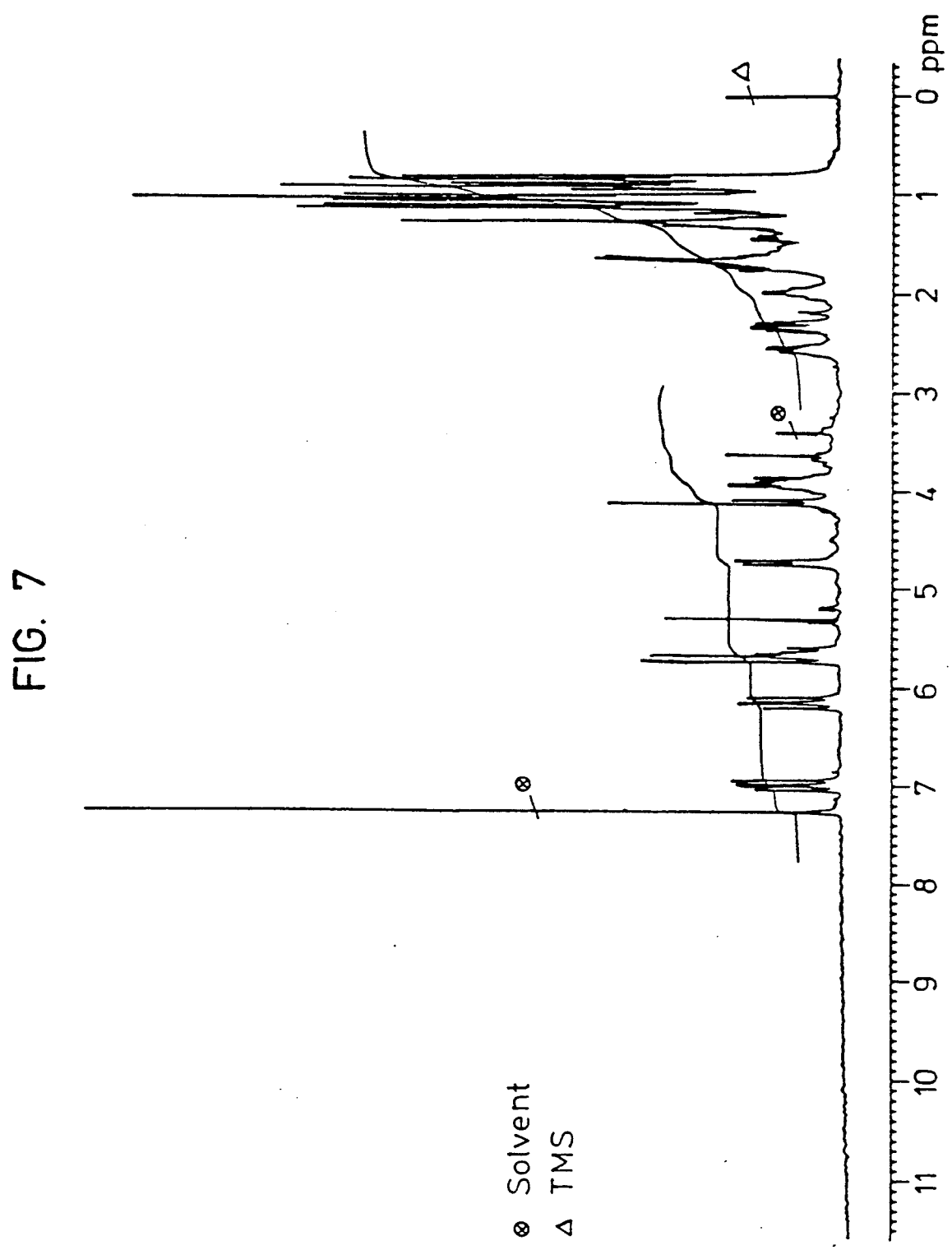
Figure 8:
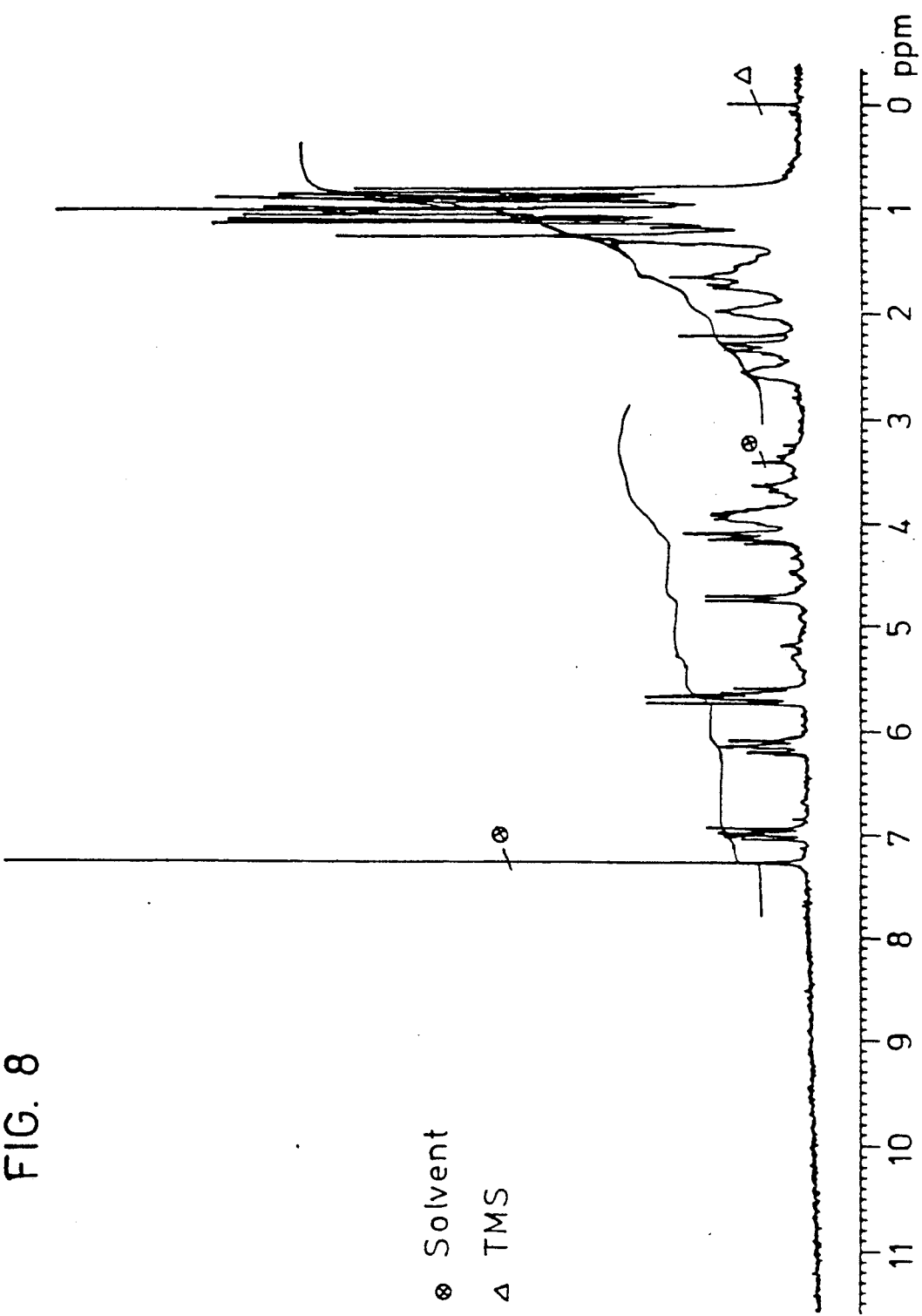

3. The $^1H$-nuclear magnetic resonance spectra, given in parts per million. These are recorded in a WM 250 from Bruker at 250 MHz on a solution of efomycin D in deuterated chloroform with tetramethylsilane as the internal standard (FIG. 7). An identical solution was recorded after shaking with deuterated water under corresponding conditions (FIG. 8).

4. The $^{13}C$-nuclear magnetic resonance spectrum, given in parts per million, according to FIG. 9.

This was recorded in a WM 250 from Bruker at 62.84 MHz on a solution of efomycin D in deuterated chloroform with tetramethylsilane as the internal standard.

5. The UV absorption maximum at 251-254 nm in methanolic solution.

2.5. The new compound efomycin F is characterized by the following chemical and physical-properties:

1. The empirical formula: $C_{48}H_{78}O_{15}$.

2. The elemental analysis: C: 63.0-65.6, H: 8.5-8.9, O: 26.5-28.5.

It must be pointed out here that the margin of error of the elemental analysis may be greater in the case of higher molecular weight naturally occurring substances than is generally customary (R. B. Woodward, Angew. Chem. 69, 50-51 (1957)).

3. The mass spectrum (Fast Atom Bombardment) molar mass + $Na^+$: 917.

4. The UV absorption maximum at 251-254 nm in methanolic solution.

5. The following absorption bands, given in $cm^{-1}$, of the IR spectrum, recorded as a KBr pressed tablet:

| | | | |
|---|---|---|---|
| 3444 | 1385 | 1150 | 745 |
| 2975 | 1304 | 1112 | |
| 2937 | 1284 | 1088 | |
| 1693 | 1259 | 1000 | |
| 1642 | 1226 | 880 | |
| 1462 | 1187 | 825 | |

Figure 10:
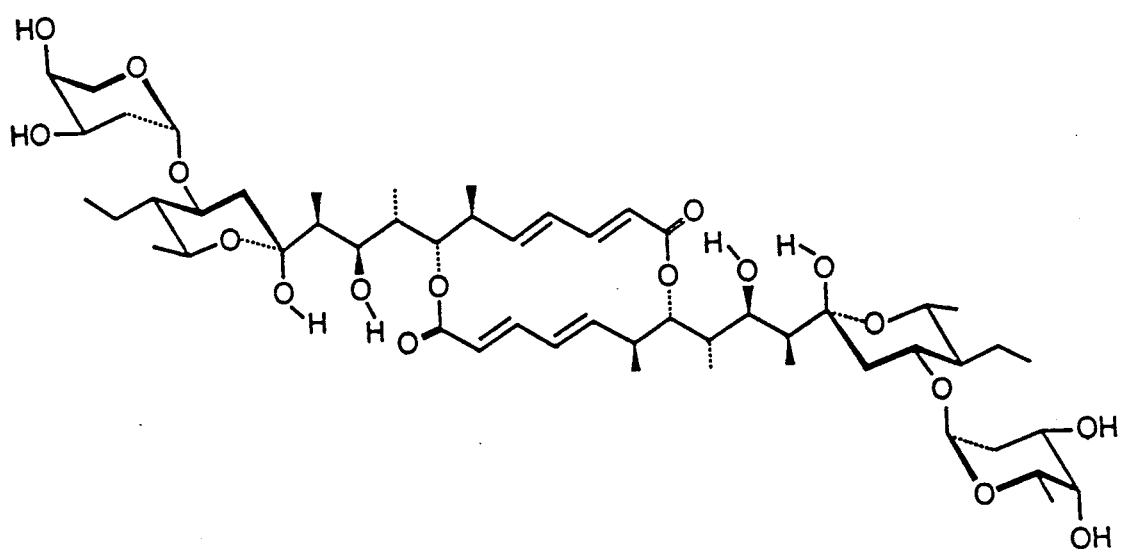

The compound efomycin E is characterized by the structural formula shown in FIG. 10.

Efomycin E is identical to azalomycin B (compare U.S. Pat. No. 3,076,746) or elaiophylin (W. Keller-Schierlein et al. Hel. Chim. Acta 64, 407-424 (1981); and K. Neupert-Laves, M. Dobler Helv. Chim. Acta 65, 262-267 (1982)) in structure and in the relative and absolute configuration of all the asymmetric carbon atoms which are configuratively stable in solution at room temperature.

3. It has furthermore been found that efomycins A, B, C, D and F according to the invention and their mixtures are obtained when suitable microorganisms of the Streptomycetaceae family are cultured under aerobic conditions in a nutrient medium containing assimilatable sources of carbon and nitrogen and mineral salts and the resulting mixture of the efomycins is isolated and separated by customary methods.

With knowledge of the properties of efomycins A, B, C, D and F, suitable strains of microorganisms which produce efomycins A, B, C, D and F can be easily and rapidly identified with the aid of customary chromatographic, spectroscopic and/or biological detection processes.

4. The Streptomyces strain BS 1261—and its mutants and variants—can be used, in particular, for carrying out the process.

This strain belongs to the Streptomycetaceae family, the Streptomyces strain from the grey series of Streptomycetes (Cinereus group).

The strain BS 1261 was deposited on Jan. 16, 1985 in the Deutsche Sammlung fur Mikroorganismen (DSM (German Collection of Microorganisms)), Griesbachstrasse 8, 3400 Göttingen, Federal Republic of Germany, under Number DSM 3200.

Taxonomic Description of the Strain BS 1261 (DSM 3200)

The taxonomic description of the strain BS 1261 has been conducted according to *Bergey's Manual of Determinative Bacteriology* 8th, (1974) and *International Journal of Systematic Bacteriology* 16, 313-340 (1966) and *The Prokaryotes* 2, 2028-2020 (1981).

1. Morphology

Good sporulation was observed on IPS media no. 2, 3, 4, 5 and 7 to 9. Substrate mycelium was predominantly formed on ISP medium No. 9 with ribose as the C source and from ISP medium No. 1 and 6.

Air Mycelium (ISP medium No. 3, 28° C., 7 days)

Color: grey (Cinereus type)
Spore chains: retinaculum-apertum type
Spores: square to rectangular, 1.4-1.8 μm-long and 1.3-1.6 μm wide, smooth (electron microscopy).

Substrate mycelium:

Color: brown

2. Physiology Data

The optimum temperature is 28° C. (on ISP medium No. 2, 5 days). The strain does not grow at 4° and 45° C. No melanine is formed. Growth is inhibited by the antibiotics erythromycin (10 μg), sulphafurazole (100 μg), streptomycin (10 μg) and novobiocin (5 μg) (ISP medium No. 2, 28° C., 2 days).

The utilization of C sources was tested on basal agar (ISP medium No. 9) in accordance with Int. J. Syst. Bact. 16, 313-340 (1966). For negative control, a comparison was made with the growth on basal agar without a C source. The following results are thereby obtained:

TABLE

| Utilization of C sources by strain BS 1261 | |
| --- | --- |
| C Source (10 g/Liter) | Growth* |
| Control (no C source) | − |
| D-glucose | + |
| L-arabinose | + |
| L-rhamnose | + |
| D-fructose | + |
| D-galactose | + |
| raffinose | + |
| D-mannitol | + |
| meso-inositol | + |
| salicin | + |
| sucrose | + |
| ribose | + |
| mannose | + |
| maltose | + |
| mellibiose | + |
| cellulose | − |
| acetate | − |

*+ = growth, − = no growth.

3. Particularly suitable medium for growth and sporulation

ISP 3 (Oatmeal Agar)

20 g of oatmeal are suspended in 1,000 ml of deionized $H_2O$ and the suspension is boiled for 20 minutes. It is then filtered, 1 ml of trace element solution for ISP3 and 18 g of agar are added, the pH value is brought to 7.2 and the mixture is autoclaved at 121° C. for 15-20 minutes.

| Trace element solution for ISP 3 | |
| --- | --- |
| $FeSO_4 7H_2O$ | 0.1 g |
| $MnCl_2.4H_2O$ | 0.1 g |
| $ZnSO_4.7H_2O$ | 0.1 g |
| deionised $H_2O$ | 100 ml |

For further media, see Int. J. Syst. Bact. 16, 313-340 (1966).

On the basis of its morphological data, strain BS 1261 isolated from a soil sample from New Zealand can be classified in the grey series of Streptomycetes (Cinereus group).

Taxonomic description: Streptomyces sp.

According to the invention, efomycins A-F are produced by the ferementation of suitable microorganisms, such as the Streptomyces strain BS 1261 or mutants or variants thereof.

The fermentation process according to the invention can be carried out with the aid of solid, semi-solid or liquid nutrient media. Aqueous-liquid nutrient media are preferably used.

The nutrient media are inoculated by generally customary methods, for example via slant tubes or flask cultures.

Culture is grown under aerobic conditions and can be carried out in accordance with the generally customary methods, such as using shaken cultures or submerse cultures. Culture is preferably carried out by the aerobic submerse process in aerated fermenters, for example in customary submerse fermentation tanks. It is possible to effect the fermentation continuously or batchwise. The batchwise procedure is preferred.

Culture is grown in nutrient media which are known for culturing microorganisms of the order Actinomycetables. The nutrient medium must contain one or more assimilatable carbon sources and nitrogen sources and mineral salts. These products should be in the form of defined individual constituents and also in the form of complex mixtures such as are represented, in particular, by biological products of various origins. Possible carbon sources are all the customary sources of carbon. Examples which may be mentioned are carbohydrates, in particular polysaccharides, such as starch or dextrins, disaccharides, such as maltose or lactose, monosaccharides, such as glucose or xylose, alcohols, such as mannitol or glycerol, and naturally occurring mixtures, such as malt extract, molasses or whey powder. Possible nitrogen sources are all the customary organic and inorganic sources of nitrogen. Examples which may be mentioned are proteins, protein hydrolysates, amino acids, nucleoside bases, such as cytosine or uracil, and soy bean flour, cottonseed flour, lentil flour, pea flour, soluble and insoluble vegetable proteins, corn steep liquor, yeast extract, peptones and meat extract, and nitrogen-containing salts, such as, for example, ammonium salts and nitrates. The mineral salts which the nutrient medium should contain give, for example, the following ions: $Mg^{++}$, $Na^+$, $K^+$, $Ca^{++}$, $NH_4^+$, $CL^-$, $SO_4^{--}$, $PO_4^{---}$ and $NO_3^-$, and ions of the customary trace elements, such as Cu, Fe, Mn, Mo, Zn, Co and Ni. If the sources of carbon or nitrogen or the water used do not contain a sufficient amount of these salts or trace elements, it is advantageous correspondingly to supplement the nutrient medium. The composition of the nutrient media can be varied within wide limits. The nature and composition of the nutrient media will in general be dependent on what constituents are in each case particularly advantageously available. The nutrient solutions in general preferably contain about 0.5 to 8%, in particular 0.6 to 6%, of sources of carbon, preferably about 0.5 to 4%, in particular 0.5 to 2%, of sources of nitrogen and preferably about 0.001 to 0.5%, in particular 0.003 to 0.3%, of mineral salts.

In carrying out the process, it may be advantageous to use only relatively small concentrations of the soluble nutrient solution constituents at the start of the culture and then to feed the culture batch fractionally in the course of the first 3 days of culture by more frequent additions of these constituents in the form of sterile, relatively concentrated solutions.

The pH value of the growing cultures should preferably be kept between about 5 and about 10, in particular between 6.5 and 8.0. Too great a drop in pH in the acid ranges can be avoided by additions of an organic or inorganic base, preferably $CaCO_3$. As is customary in fermentation technology, the pH can also be automatically regulated by injecting sterile organic or inorganic acids, for example $H_2SO_4$, or sterile alkalis, for example NaOH, into the culture solution at intervals.

It is advantageous to ensure that the microorganisms are brought into sufficient contact with oxygen and the nutrients. This can be effected by the generally customary methods, such as shaking and stirring.

The culture temperature can be between about 24° C. and about 34° C., preferably between 26° C. and 32° C., it is particularly preferably about 28° C. The duration of culture can be varied greatly, the composition of the nutrient medium and the culture temperature, for example, playing a part. The particular optimum conditions can easily be determined by any expert in the microbiological field.

It has been found that the amount of compounds according to the invention which become enriched in the culture broth in general reaches its maximum about 1 to 10, preferably about 4 to 7, days after the start of culture. The desired end product of the fermentation can be determined with the aid of investigation by thin layer chromatography and high pressure liquid chromatography or biological test methods.

As is generally customary in microbiological processes, foreign infections of the culture media should be avoided. The customary measures are taken for this, such as sterilization of the nutrient media, the culture vessels and the air required for aeration. Steam sterilization and dry sterilization can be used, for example, for sterilization of the devices, it being possible for the temperatures to be preferably 100° to 140° C., in particular 120° to 130° C.

If an undesirable amount of foam is formed during culture, the customary chemical foam suppressants can be added, for example liquid fats and oils, such as oil-in-water emulsions, paraffins, higher alcohols, such as octadecanol, silicone oils and polyoxyethylene and polyoxypropylene compounds (for example in amounts of up to about 1%). Foam can also be suppressed or eliminated with the aid of the customary mechanical devices (which use, for example, centrifugal forces).

The compounds according to the invention can be isolated from the culture medium by generally customary physico-chemical methods. Isolation can be effected, for example, in accordance with the customary extraction processes, precipitation processes and/or chromatography processes. The isolated substances can also be subjected to fine purification with the aid of the methods mentioned. However, in many cases fine purification is not necessary, since any small amounts of impurities present do not adversely influence the efficacy of the compounds. During all the isolation and purification operations, care should be taken that the pH values are in the neutral range. pH values between 7 and 8 are preferably maintained. Inorganic and organic bases, such as alkali metal bases, for example NaOH or KOH, or organic amines, such as triethylamine; inorganic acids, such as, for example, HCL, and organic acids, such as, for example, acetic acid, can be used to establish the pH value.

The customary physico-chemical methods, for example measurement of a characteristic band in the spectrum or of the $R_f$ values, determination of the antibacterial activity and the like, can be used to discover, in the abovementioned isolation and purification methods, the fractions in which the compounds according to the invention are present in the highest concentration or purity. These methods can also be used to discover suitable microorganisms for the production of efomycins in routine processes.

Isolation and purification of the compounds according to the invention can be carried out as follows, for example in the case where a liquid aqueous nutrient medium is used:

Since the efomycins are to be found both in the culture supernatant and in the mycelium, they can be isolated from the fermentation batch with the aid of customary extraction processes, precipitation processes and/or chromatography processes and, if appropriate, purified. Chromatography can be carried out in the form of column chromatography. High pressure liquid chromatography (HPLC) can also be highly successfully employed. Adsorbents which can be used are the customary inorganic or organic adsorbents, such as, for example, silica gel, magnesium silicate, active charcoal, cellulose, cellulose derivatives, synthetic resins, such as polyamides, for example acetylated polyamide, dextran gels or modified dextran gels. Possible eluants are the most diverse solvents or solvent mixtures in which the compounds according to the invention are soluble. Ethyl acetate, chloroform and methanol or mixtures thereof (for example mixtures of chloroform and methanol or of ethyl acetate and chloroform) are preferably employed.

Chromatography processes, for example non-specific adsorption onto sorbents, such as silica gel, or, on the other hand, gel diffusion chromatography, are preferably used for isolating the compounds according to the invention. These are the methods known from the purification of naturally occurring substances which are poorly water-soluble.

The compounds according to the invention can be obtained from their solutions by the customary methods, for example evaporation of the solvent, freeze-drying and the like.

In a preferred embodiment, the mycelium is separated off from the culture broth, preferably by centrifugation, and extracted several times, preferably twice, with a water-miscible solvent. Solvents which can be used are ($C_1$-$C_4$)-alkyl alcohols and $C_{1-4}$-ketones, particularly preferably acetone. The aqueous-organic solution is concentrated in vacuo, for example to about 1/20 of the volume of the culture broth, and freeze-dried.

This crude product is suspended in water and the efomycins are extracted with a water-immiscible solvent, such as, for example, chlorohydrocarbons, such as chloroform, esters of acetic acid or ketones, The efomycins can be isolated from this extract by customary chromatographic methods, preferably chromatography on silica gel.

The efomycins can also be extracted from the culture filtrate by extraction with a water-immiscible solvent, such as, for example, ethyl acetate, methylene chloride or chloroform.

They can furthermore be bonded to non-specific adsorber resins based on polystyrene (for example Amberlite XAD from Roehm and Haas or Lewatit OC 1031 from Bayer). Desorption is carried out fractionally, by mixtures of water and organic solvents, in particular water/methanol. The fractions determined as active by a test against Staphylococcus aureus 1756 are concentrated at 30°-35° C. under reduced pressure until the organic solvent has been removed completely, and the residue is suspended in about 1/100 of the volume of the culture filtrate and the suspension is freeze-dried.

The lyophilizate is suspended again in water and extracted, preferably with ethyl acetate or other water-immiscible solvents. The efomycins are obtained from the extract by customary chromatographic methods, preferably chromatography on silica gel.

The compounds according to the invention exhibit a good antibacterial action, above all against Gram-positive germs. Their suitability for the prevention and curing of dysentery in pigs should be mentioned in particular.

The active compounds are used as performance promoters in animals for promoting and accelerating growth, and milk and wool production, for improving feed utilization and meat quality and for shifting the meat/fat ratio in favor of meat. The active compounds also prevent and treat ketosis. The active compounds are used on livestock animals, pets and hobby animals.

The livestock and breeding animals include mammals, such as, for example, cattle, pigs, horses, sheep, goats, rabbits, hares, fallow deer and furbearing animals, such as mink and chinchilla, fowl, such as, for example, chickens, geese, ducks, turkeys and pigeons, fish, such as, for example, carp, trout, salmon, eels, tench and pike, and reptiles, such as, for example, snakes and crocodiles.

The pets and hobby animals include mammals, such as dogs and cats, birds, such as parrots and canaries, and fish, such an ornamental fish and aquarium fish, for example goldfish.

The active compounds are employed independently of the sex of the animals, during all the growth and performance phases of the animals. The active compounds are preferably employed during the intensive growth and performance phase. The intensive growth and performance phases last from one month up to ten years, depending on the species of animal.

The amount of the active compounds administered to the animals to achieve the desired effect can be varied substantially, because of the advantageous properties of the active compound. It is preferably about 0.001 to 500 mg/kg, in particular 0.01 to 5 mg/kg of body weight per day. The appropriate amount of the active compound and the appropriate duration of the administration depend, in particular, on the species, age, sex, growth and performance phase, state of health and nature of housing and feeding of the animals and can easily be determined by any expert.

The active compounds are administered to the animals by the customary methods. The nature of the administration depends, in particular, on the species, behavior and state of health of the animals.

The active compounds can be administered once. However, the active compounds can also be administered temporarily or continuously throughout the entire or throughout part of the growth and performance phase.

In the case of continuous administration, they can be used once or several times daily at regular or irregular intervals.

Administration is oral or parenteral in formulations suitable for this purpose or in the pure form.

The active compounds can be present in the formulations by themselves or as a mixture with other performance-promoting active compounds, mineral feedstuffs, trace element compounds, vitamins, non-protein compounds, colorants, antioxidants, aroma substances, emulsifiers, lubricants, preservatives and pressing auxiliaries.

Other performance-promoting active compounds are: for example, antibiotics, such as tylosin, virginiamycin and monensin. Mineral feedstuffs are, for example, dicalcium phosphate, magnesium oxide and sodium chloride.

Trace element compounds are, for example, iron fumarate, sodium iodide, cobalt chloride, copper sulphate and zinc oxide.

Vitamins are, for example, vitamin A, vitamin D3, vitamin E, B vitamins and vitamin C.

Non-protein compounds are, for example, biuret and urea.

Colorants are, for example, carotinoids, such as citranaxanthine, zeaxanthine and capsanthine.

Antioxidants are, for example, ethoxyquine and butylhydroxy-toluene.

Aroma substances are, for example, vanillin.

Emulsifiers are, for example, esters of lactic acid and lecithin.

Lubricants are, for example, sodium stearate and calcium stearate.

Preservatives are, for example, citric acid and propionic acid.

Pressing auxiliaries are, for example, ligninsulphonates and cellulose ethers.

The active compounds can also be administered together with the feed and/or drinking water.

Feed includes individual feedstuffs of vegetable origin, such as hay, beet and cereal by-products, individual feedstuffs of animal origin, such as meat, fats, milk products, bone meal and fish products, and the individual feedstuffs such as vitamins, proteins, amino acid, for example DL-methionine, and salts, such as lime and sodium chloride. Feed also includes feedstuff supplements, finished feedstuffs and mixed feedstuffs. These contain individual feedstuffs in a composition which guarantee a balanced nutrition in respect of energy and protein supply and supplies of vitamins, mineral salts and trace elements.

The concentration of the active compound in the diet is usually about 0.01–500 ppm, preferably 0.1–50 ppm.

The active compounds can be added to the feed as such or in the form of premixes or feed concentrates. Those contain from about 1–800 g active compound per kg of premix or feed concentrate.

An example of the composition of a high-grain ration for cattle is the following: coarse ground corn 69.95%, ground corncobs 10%, soybean meal 8%, alfalfa meal 5%, molasses 5%, urea 0.6%, dicalcium phosphate 0.5%, calcium carbonate 0.5%, salt 0.3%, vitamin A and $D_2$ premix 0.07%, vitamin E premix 0.05% and trace mineral premix 0.03%. The premix containing the active compounds can be added to such a ration.

It is not absolutely necessary to use purified and isolated efomycins A–F. It is also possible to employ the mixtures obtained during their preparation or even the culture broth obtained or the mycelium, without purification, if appropriate after drying. For many purposes it is also sufficient to employ crude forms of the active compounds according to the invention and their mixtures without prior fine purification.

Figure 2:
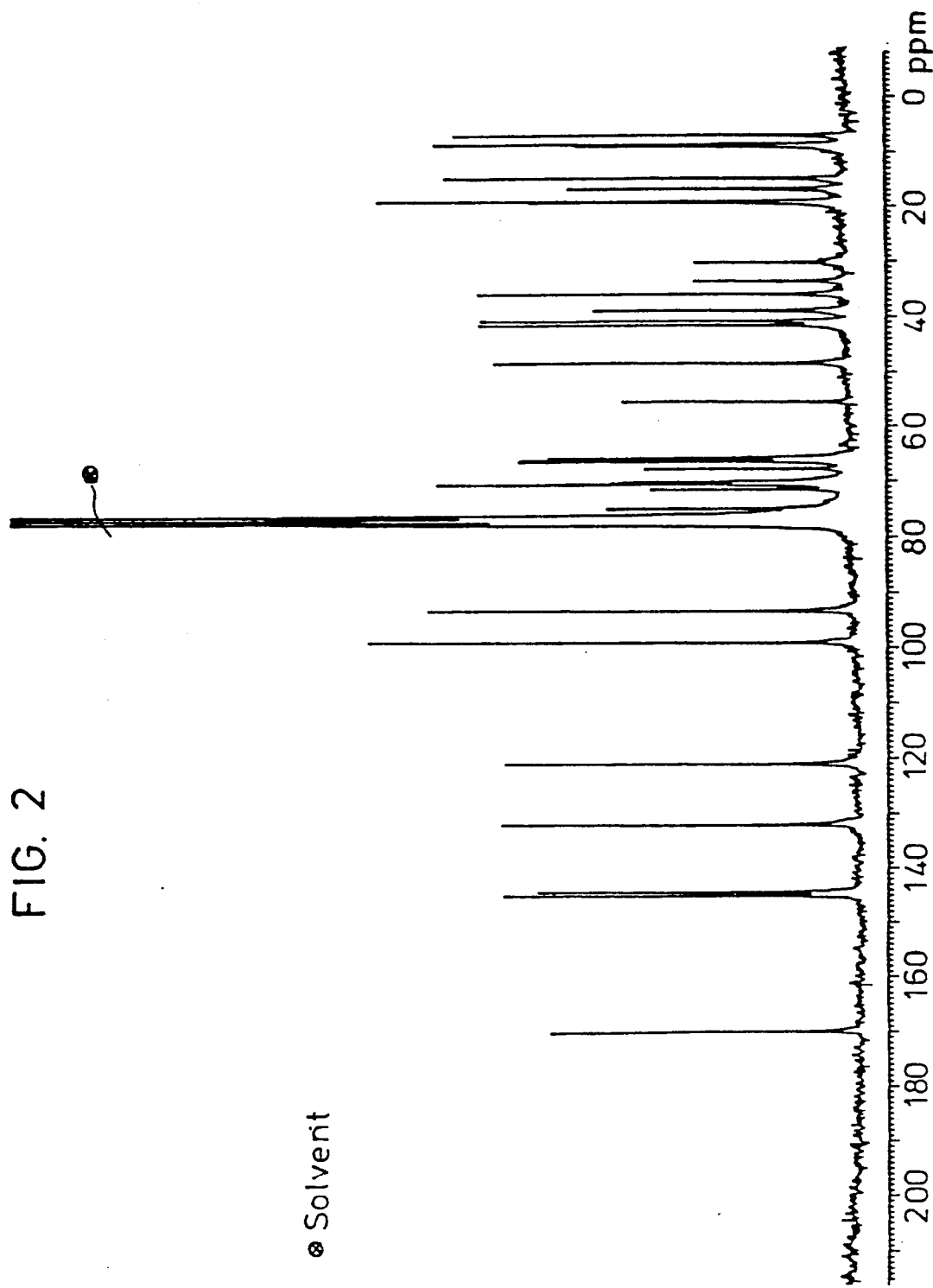
Figure 3:
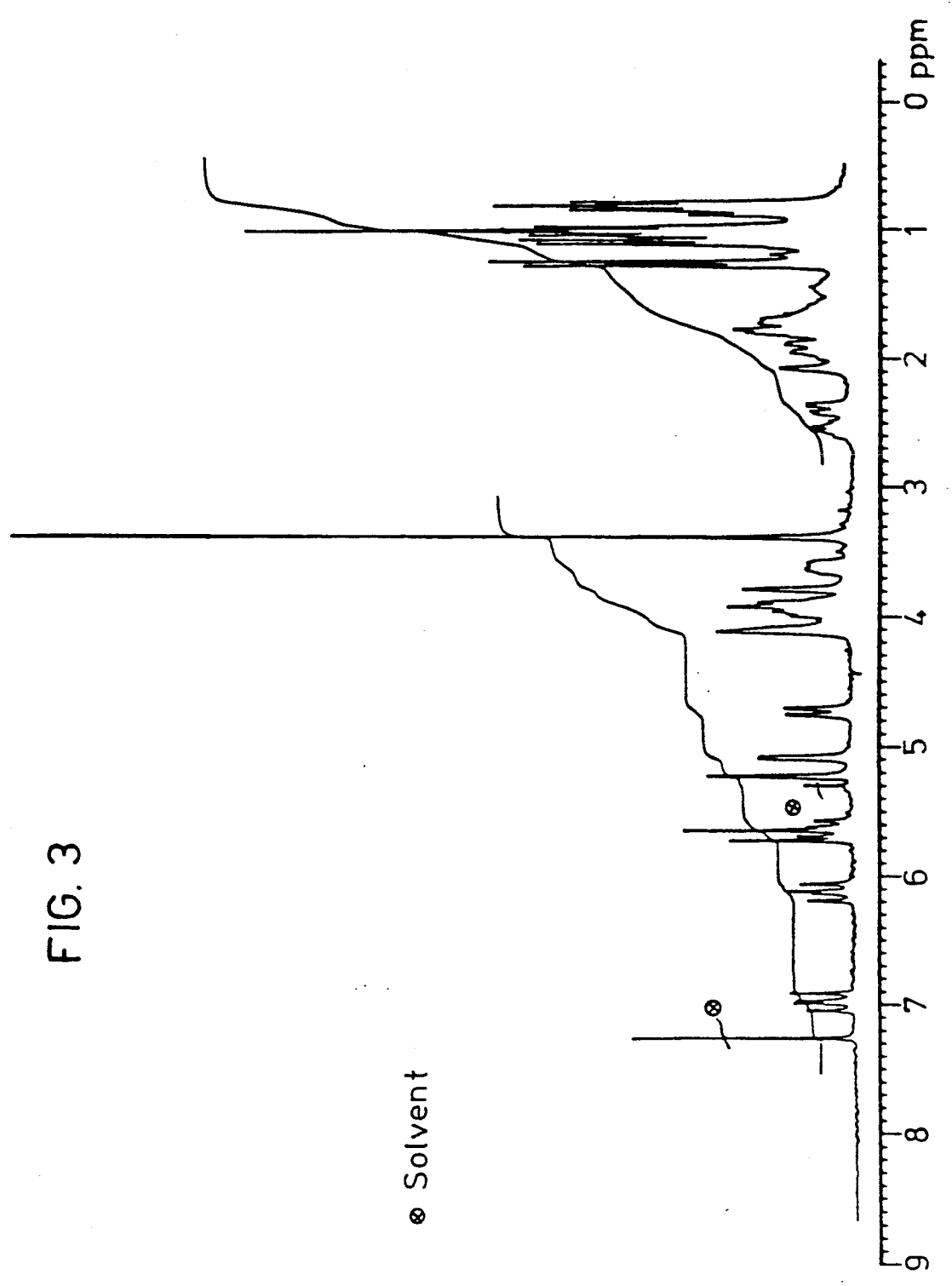
Figure 4:
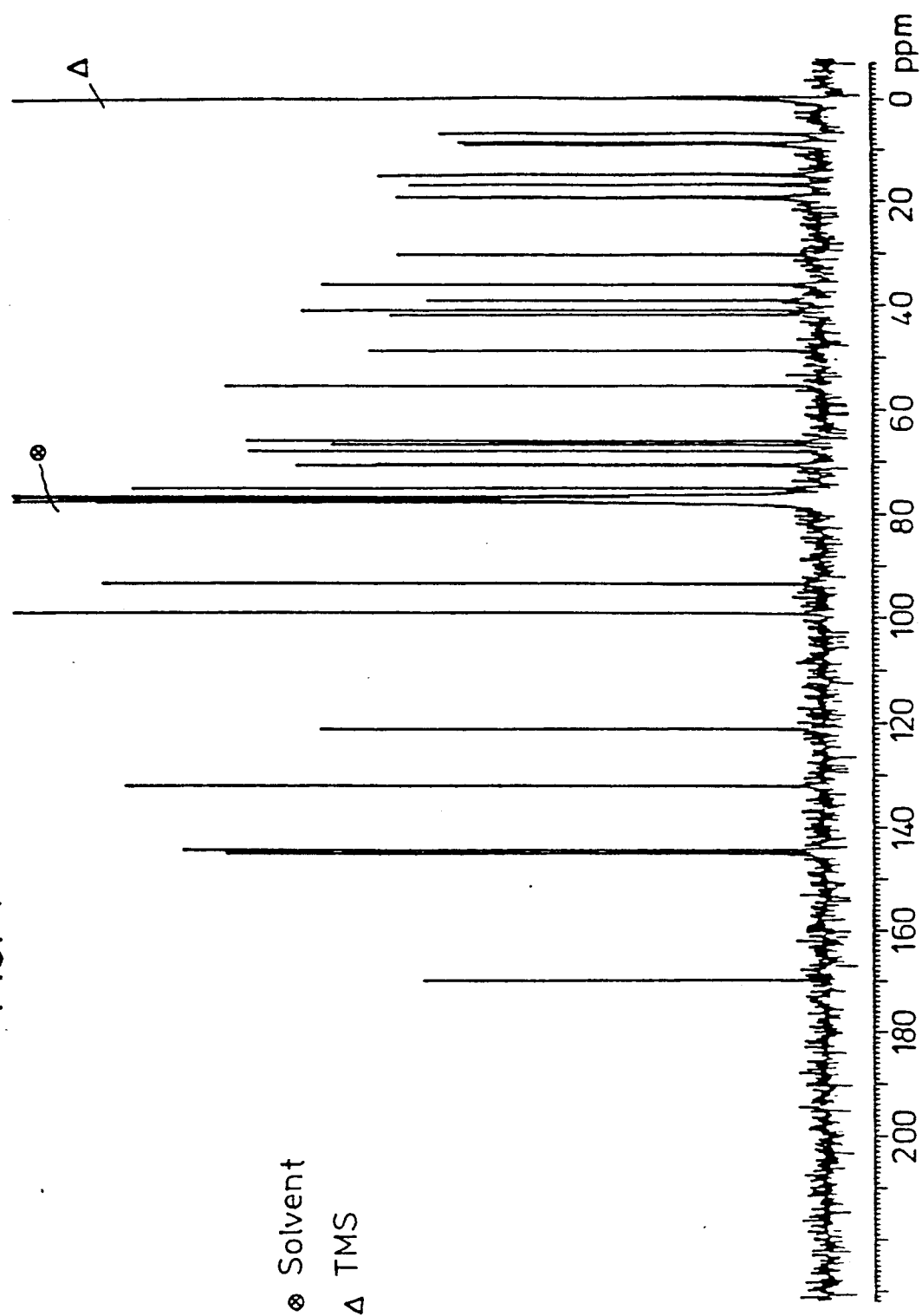
Figure 5:
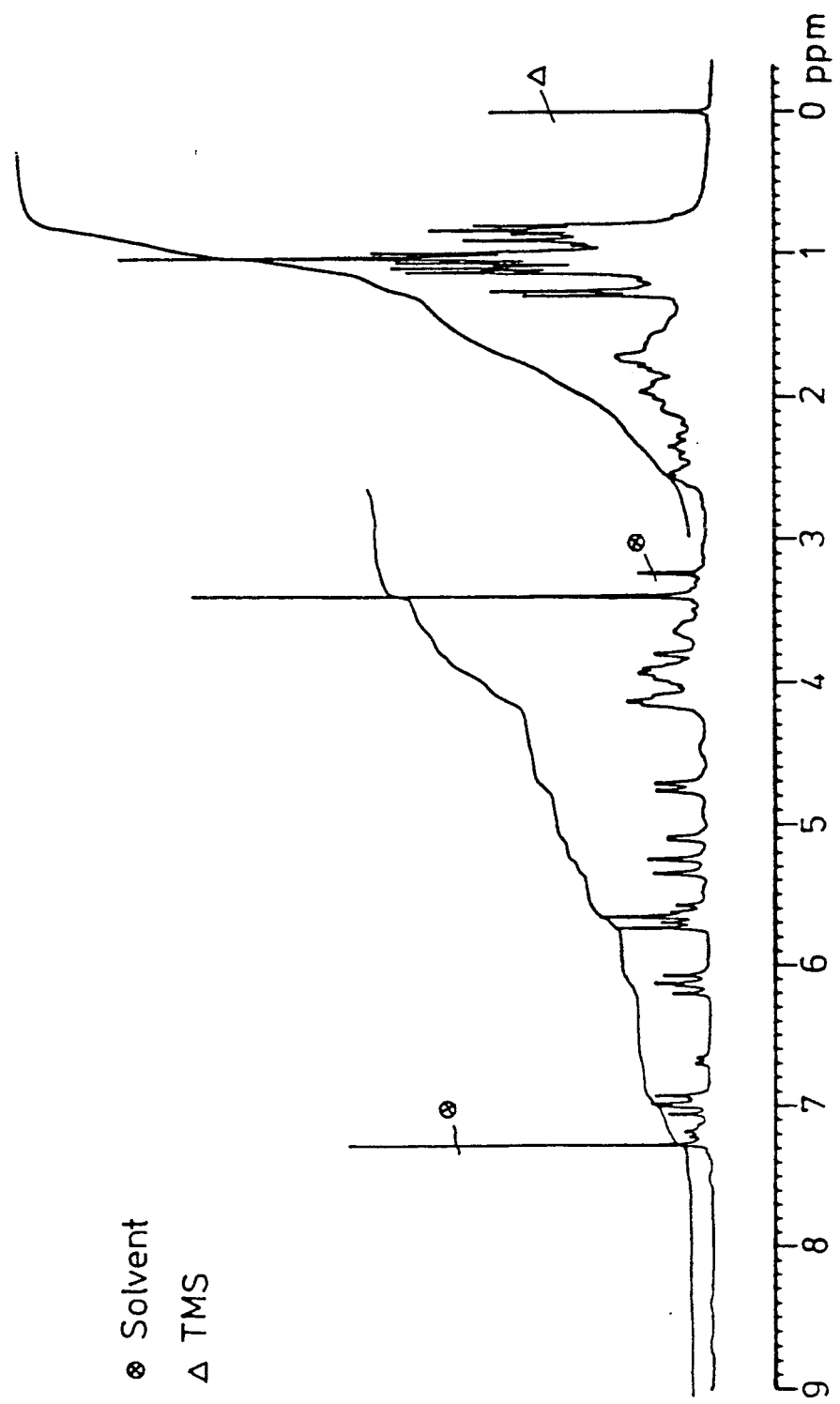
Figure 6:
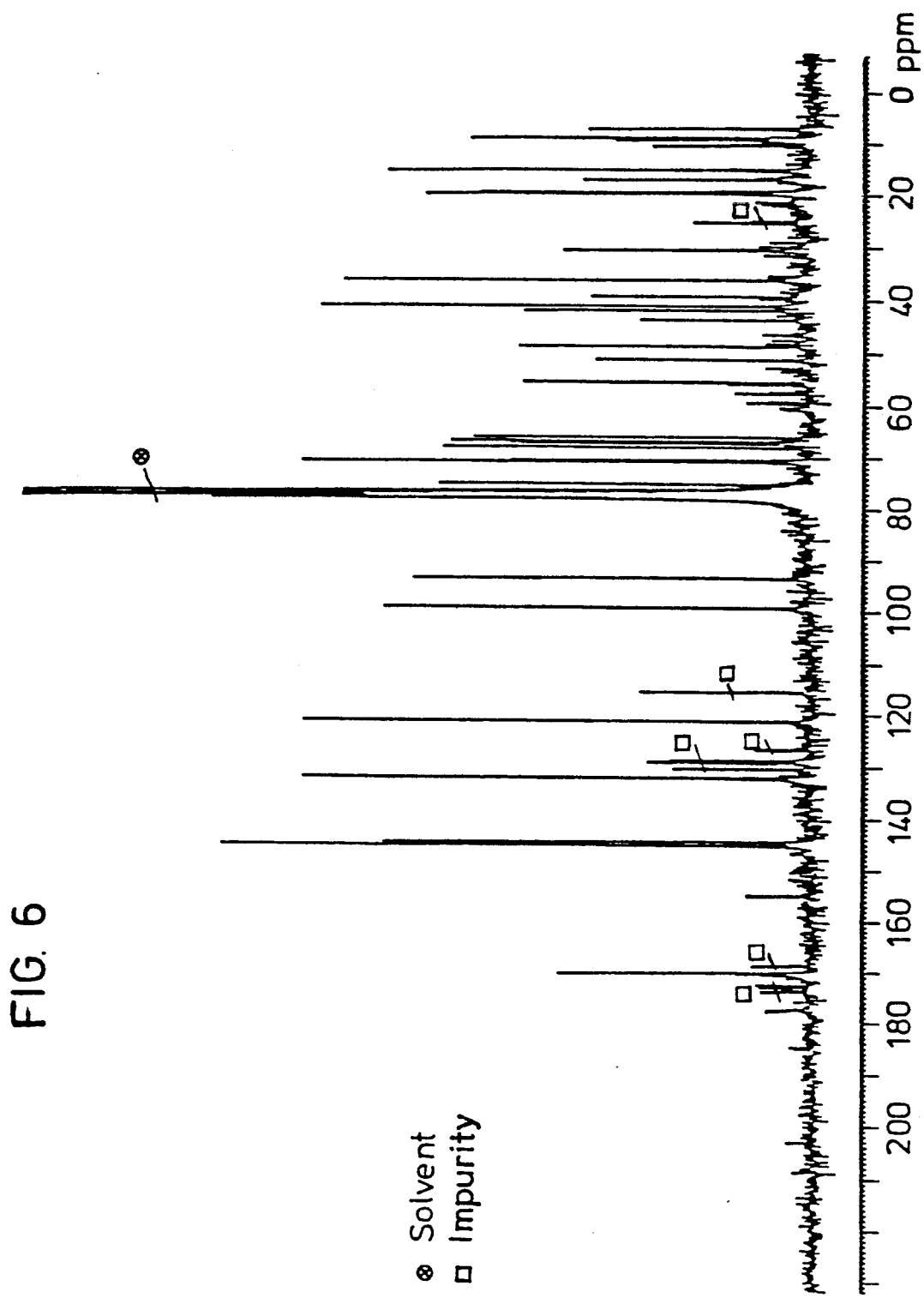
Figure 9:
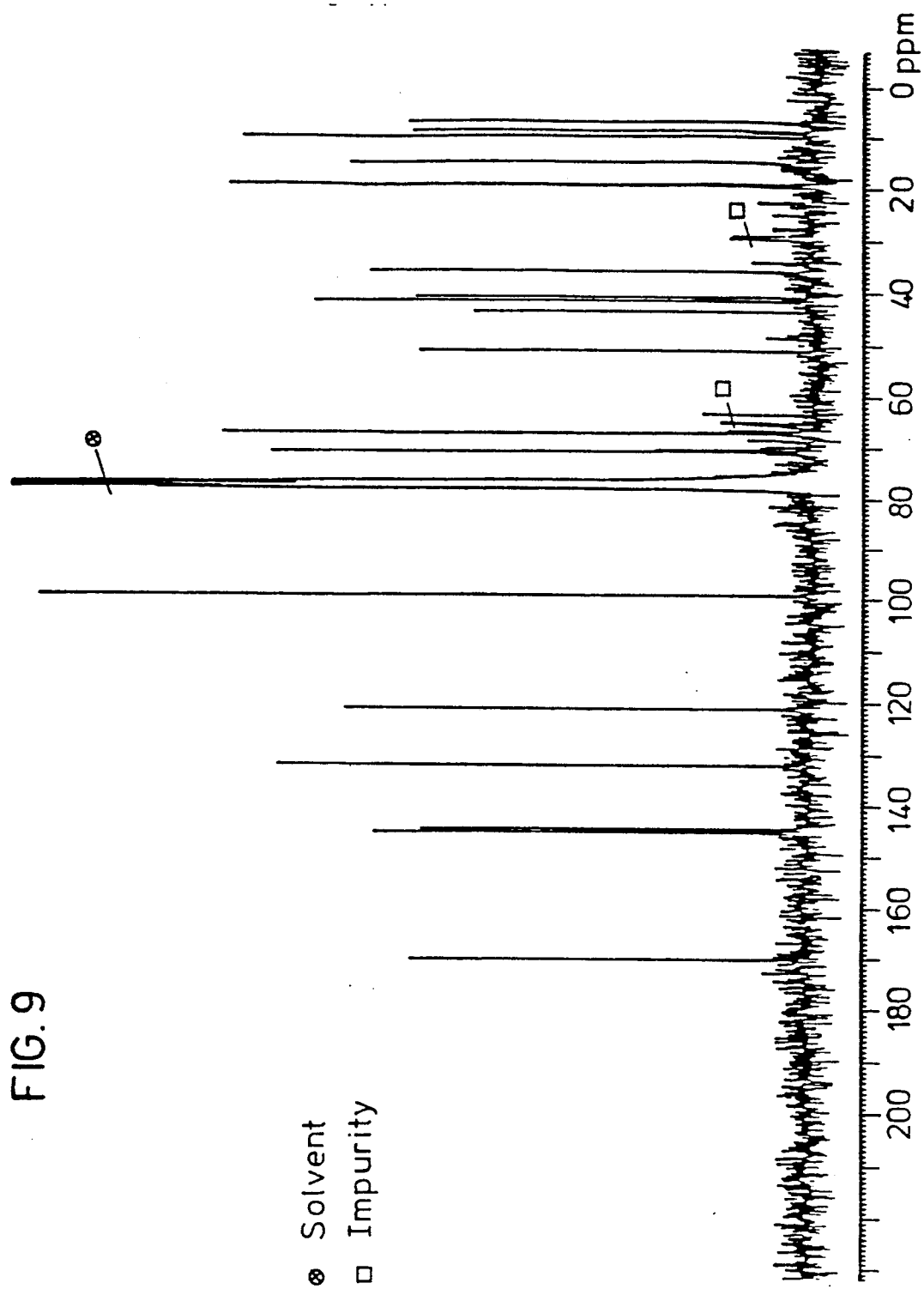
Figure 11:
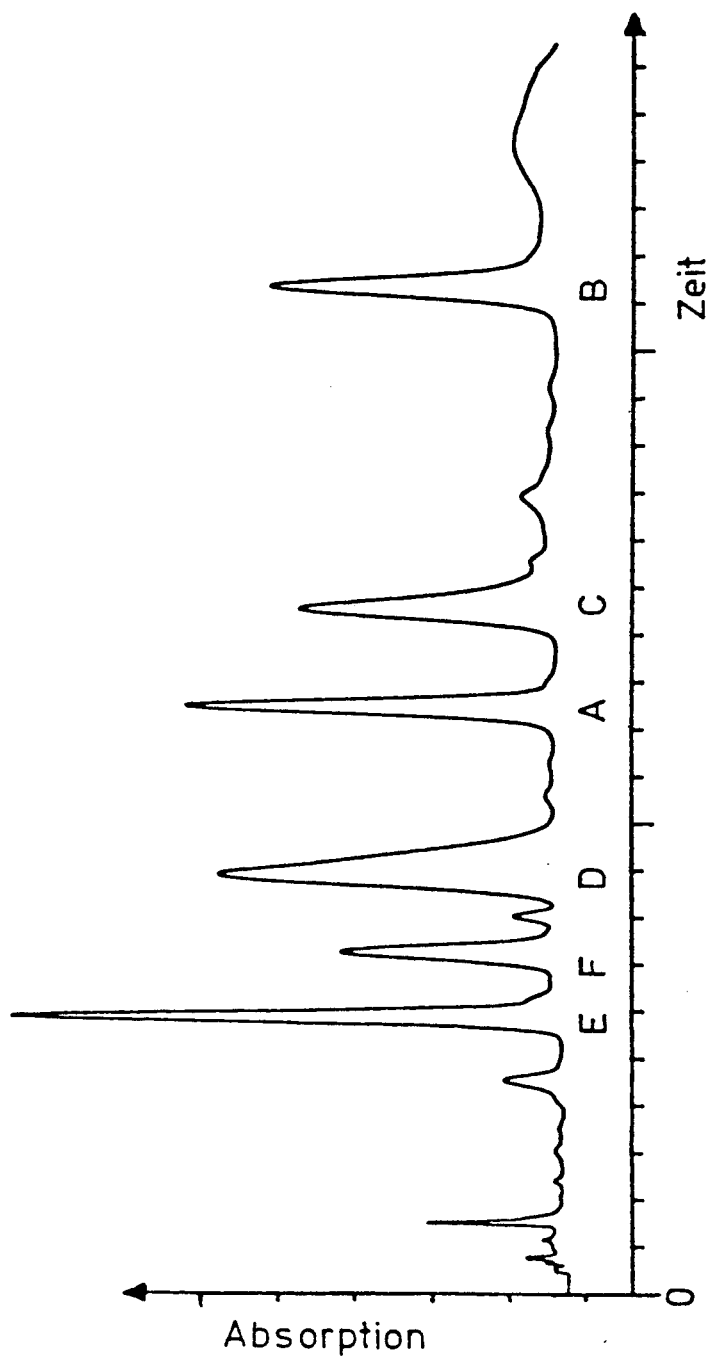

In the accompanying drawings,

FIG. 1 is a $^1$H—NMR spectrum of efomycin A;
FIG. 2 is a $^{13}$C—NMR spectrum of efomycin A;
FIG. 3 is a $^1$H—NMR spectrum of efomycin B;
FIG. 4 is a $^{13}$C—NMR spectrum of efomycin B;
FIG. 5 is a $^1$H—NMR spectrum of efomycin C;
FIG. 6 is a $^{13}$C—NMR spectrum of efomycin C;
FIG. 7 is a $^1$H—NMR spectrum of efomycin D in deuterated chloroform;
FIG. 8 is a $^1$H—NMR spectrum of efomycin D in deuterated water;
FIG. 9 is a $^{13}$C—NMR spectrum of efomycin D;
FIG. 10 is a structural formula of efomycin E; and
FIG. 11 is a chromatogram of a mixture of efomycin components A to E.

The preparation and biological action of the new compounds according to the invention can be illustrated by the following examples:

EXAMPLE 1

150 ml of sterile nutrient solution (CASO® from Merck, Darmstadt) of the composition:

| peptone from casein | 15 g |
| peptone from soy bean flour | 5 g |
| glucose | 2.5 g |
| NaCl | 5 g |
| water to | 1,000 ml | are inoculated in a 1 liter conical flask with vegetative cells of the Streptomyces strain BS 1261. The culture is incubated at 28° C. on a rotary shaking machine for 3–4 days. The grown cultures are used as the inoculum for further fermentation batches.

20 liters of nutrient solution of the composition described above and 20 ml of anti-foaming agent (SAG 5693, Union Carbide) are introduced into a fermenter (30 liters) with a stirrer and aeration device and are sterilized at 120° C. for 30 minutes. After the solution has been cooled, the fermenter is inoculated with the contents of 2 flasks of the shaken cultures of the Streptomyces strain BS 1261 obtained as described above, aerated with 10 liters of sterile air per minute at 250 revolutions of the stirrer per minute and fermented at a temperature of 28° C. under a blanketing pressure of 0.5 bar.

The fermentation is ended after 1–2 days and the contents are used to seed a 300 liter tank fermentor.

EXAMPLE 2

Tank Fermentation 300 liters of the nutrient solution of the following compositions

| skimmed milk powder | 10 g |
| yeast autolysate | 1,5 g |
| dextrin | 40 g |
| D-glucose | 5 g |
| anti-foaming agent (SAG 5693 Union Carbide) | 1 ml |
| to | 1000 ml $H_2O$ | are adjusted to about pH 7 in a 300 liter fermentor, sterilized at 121° C. for 60 minutes, cooled to 28° C. and inoculated with 20 liters of the inoculum obtained according to Example 1. The fermentation is conducted at 28° C. with stirring at 100 revolutions per minute and aeration at 100 liters of sterile air per minute under a blanketing pressure of 1.0 bar, until after 3–4 days the Efomycin compounds are produces. The culture is then harvested.

EXAMPLE 3

The culture broth, obtained according to Example 2, of a 200 liter fermentation is separated at pH 7–7.5 and at 200–250 liters/hour in a Westfalia separator. The mycelium is stirred with twice the volume of acetone at room temperature for 30 minutes and centrifuged. The residue is stirred again with twice the volume of acetone and centrifuged. The combined centrifugates are concentrated under reduced pressure at a bath temperature of 40° C. 20 liters of water are added to the concentrate and the mixture is freeze-dried, 540 g of the crude efomycin mixture according to the invention being obtained with a content of about 5% of efomycins.

EXAMPLE 4

60 g of the crude active compound mixture obtained according to Example 3 are suspended in 3 liters of water and the suspension is extracted three times with 400 ml of chloroform each time. The combined organic phases are dried over anhydrous sodium sulphate and filtered and the filtrate is concentrated to a volume of 100 ml under reduced pressure at a bath temperature of 35° C. The concentrated solution is allowed to run into 2 liters of heptane, with stirring. After stirring for a further 30 minutes, the mixture is filtered, 3.6 g of residue with an efomycin mixture content of about 80% being obtained.

EXAMPLE 5

3.3 g of the efomycin mixture prepared according to Example 4 are dissolved in 0 ml of chloroform, the solution is applied to a Lobar ® pre-packed column Lichroprep Si 60 (40-63 μm, Merck size (C), equilibrated in chloroform, and the column is eluted fractionally with a mixture of chloroform and 7% of methanol. Analysis of the eluate by thin layer chromatography (Merck 5715, chloroform 7% of methanol, detection by fluorescence quenching at 254 nm), gives, arranged according to decreasing $R_F$ values, three fractions I, II and III, which are evaporated to dryness separately in vacuo at about 35° C.

Fraction I contains 480 mg of a product mixture, which is separated by thick layer chromatography on silica gel plates (Merck 13 895 with ethyl acetate as the mobile phase into three components which, on the basis of increasing $R_F$ values, are designated efomycin B (160 mg yield), efomycin C (60 mg yield) and efomycin D (40 mg yield).

Fraction II contains 950 mg of a product mixture, which is separated by thick layer chromatography on silica gel plates (Merck 13 895) with ethyl acetate as the mobile phase, into two components which, according to increasing $R_F$ values, are designated efomycin A (510 mg yield) and efomycin F (320 mg yield).

Fraction III contains 1.6 g of efomycin E as the evaporation residue, which can be recrystallized from methanol.

The degrees of purity of the efomycin components A to E thus obtained can be determined in approximation by means of HPLC (Nova Pak ® column, C-18 18.4 μm, 3.9×150 mm; Waters; mobile phase: 5 mM citric acid with 45-65% of acetonitrile added as a gradient in 18 minutes; flow rate 1.5 ml/min) by extinction measurements at a detector wavelength of 254 nm and/or 208 nm. They are accordingly at least 80-85% for each component. A corresponding chromatogram of a mixture of efomycin components A to E is shown in FIG. 11.

EXAMPLE A

Rumen fluid was removed through a rumen fistula from a wether which received 650 g of coarsely ground finished sheep feed and 250 g of dried green cobs per day. The finished feed was administered by an automatic feeder in 12 equal portions at intervals of two hours, and the cobs were administered in 2 equal portions at 8.30 a.m. and 4.15 p.m. Immediately after being obtained, the rumen fluid was subjected to the following treatment: 2.5 ml of the rumen inoculum were pipetted into a test tube which had a volume of 13 ml and was gassed with carbon dioxide and furthermore contained the following: 100 mg of finely ground finished sheep feed, 7.5 ml of buffer solution and 0.5 ml of a solution with or without the compound according to the invention.

The composition of the buffer solution which was saturated with carbon dioxide before the start of the experiment was as follows:

| | |
|---|---|
| $Na_2HPO_4$ | 4.61 g per liter of water |
| $NaHCO_3$ | 12.25 g per liter of water |
| NaCl | 0.59 g per liter of water |
| KCl | 0.71 g per liter of water |
| $MgCl_2$ | 0.32 g per liter of water |
| $CaCl_2$ | 0.13 g per liter of water |

0.5 ml of a solution which contained the desired amount of the compounds according to the invention in 5 percent strength aqueous ethanol was added to this mixture. Thereafter, the total volume of the fermentation mixture was 10.5 ml. Each test tube was closed with a Bunsen stopper and incubated at 39° C. After 2, 4, 6 and 8 hours, the batches were shaken manually. After incubation for 24 hours, 1.0 ml of the fermentation liquid was taken out of the batches and pipetted into an Eppendorf vessel containing 0.2 ml of 10% strength phosphoric acid (containing 5.7 μmol of 2-methylvaleric acid). The samples were centrifuged at 11,000 g and the volatile fatty acid concentrations from the supernatant were determined by gas chromatography.

The ratio of acetic acid to propionic acid was determined for each experiment. The value obtained in the negative controls was set at 100 and the deviations were given in relation to this. The more propionic acid formed, the lower the ratio of acetic acid to propionic acid and the smaller the ratio figure in comparison with the control (low ratio figure=reduced acetic acid/propionic acid ratio=improved feed utilization).

In addition, the deviations of total fatty acids in comparison with the control (=100) were stated for each experiment.

The results are summarized in the following tables:

TABLE A

| | Mixture of all efomycin components | |
|---|---|---|
| Amount (μg/batch) | Acetic acid/ propionic acid ratio | Total fatty acids |
| Control | 100 | 100 |
| 20 | 96.7 | 107.1 |
| 50 | 66.9 | 105.4 |
| 100 | 42.5 | 105.8 |
| 250 | 35.6 | 104.9 |
| 500 | 36.7 | 104.8 |

TABLE B

| | Efomycin A | |
|---|---|---|
| Amount (μg/batch) | Acetic acid/ propionic acid ratio | Total fatty acids |
| Control | 100 | 100 |
| 20 | 89.9 | 99.4 |
| 50 | 73.3 | 107.3 |
| 100 | 54.8 | 106.7 |
| 250 | 48.7 | 109.5 |
| 500 | 48.7 | 107.2 |

TABLE C

| | Efomycin E | |
|---|---|---|
| Amount (μg/batch) | Acetic acid/ propionic acid ratio | Total fatty acids |
| Control | 100 | 100 |
| 20 | 77.8 | 105.7 |

TABLE C-continued

| Amount (μg/batch) | Efomycin E Acetic acid/ propionic acid ratio | Total fatty acids |
|---|---|---|
| 50 | 53.6 | 107.5 |
| 100 | 38.8 | 109.3 |
| 250 | 36.6 | 105.0 |
| 500 | 36.1 | 104.1 |

EXAMPLE B

Twenty-four Holstein-Friesian cows were selected in order to determine the effects of the compounds according to the invention on milk yield. Six cows received in each case 1000 mg of a mixture of all efomycin components daily, six received in each case 1000 mg of efomycin A daily, six received in each case 1000 mg of efomycin E daily and six cows formed the negative controls. The compounds according to the invention were added in the form of a premix to the finished feed of the 18 test cows. All the cows received a ration containing 45% of corn, 20% of lucerne hay and 35% of finished feed. The feed intake, milk production and milk composition (content of fat, protein and lactose) were measured daily for 12 weeks. The experiment started four weeks after calving. Good results were achieved in this experiment, that is to say an increased milk production with no influence on the milk composition.

It will be understood that the specification and examples are illustrative but not limitative of the present invention and that other embodiments within the spirit and scope of the invention will suggest themselves to those skilled in the art.

We claim:

1. At least one member selected from the group consisting of efomycin A, B, C, D and F.
2. A compound according to claim 1, wherein such compound is efomycin A.
3. A compound according to claim 1, wherein such compound is efomycin B.
4. A compound according to claim 1, wherein such compound is efomycin C.
5. A compound according to claim 1, wherein such compound is efomycin D.
6. A compound according to claim 1, wherein such compound is efomycin F.
7. An animal feed supplement comprising a feed base and a performance promoting effective amount of at least one promoter selected from the group consisting of efomycin A, B, C, D, E and F.
8. A feed supplement according to claim 7, wherein said promoter comprises efomycin A.
9. A feed supplement according to claim 7, wherein said promoter comprises efomycin B.
10. A feed supplement according to claim 7, wherein said promoter comprises efomycin C.
11. A feed supplement according to claim 7, wherein said promoter comprises efomycin D.
12. A feed supplement according to claim 7, wherein said promoter comprises efomycin E.
13. A feed supplement according to claim 7, wherein said promoter comprises efomycin F.
14. A method of promoting the performance of an animal which comprises administering to said animal a performance promoting effective amount of at least one promoter selected from the group consisting of efomycin A, B, C, D, E and F.
15. The method according to claim 14, wherein said promoter comprises efomycin A.
16. The method according to claim 14, wherein said promoter comprises efomycin B.
17. The method according to claim 14, wherein said promoter comprises efomycin C.
18. The method according to claim 14, wherein said promoter comprises efomycin D.
19. The method according to claim 14, wherein said promoter comprises efomycin E.
20. The method according to claim 14, wherein said promoter comprises efomycin F.

* * * * *